United States Patent
Delbos et al.

(10) Patent No.: US 8,297,128 B2
(45) Date of Patent: Oct. 30, 2012

(54) DEVICE FOR DETERMINING A PHYSICAL VALUE OF A LIQUID FLOWING IN A PIPE

(75) Inventors: Cecile Delbos, Eschau (FR); Jean-Louis Weissenbach, Ville (FR); James Vigna, North Andover, MA (US); Martin Morrissey, Beverly, MA (US); Rene Reinbigler, Kirchheim (FR)

(73) Assignee: EMD Millipore Corporation, Billerica, MA (US)

( * ) Notice: Subject to any disclaimer, the term of this patent is extended or adjusted under 35 U.S.C. 154(b) by 267 days.

(21) Appl. No.: 12/698,624

(22) Filed: Feb. 2, 2010

(65) Prior Publication Data
US 2011/0041619 A1    Feb. 24, 2011

(30) Foreign Application Priority Data
Mar. 13, 2009    (FR) ..................... 09 51600

(51) Int. Cl.
*G01L 7/00* (2006.01)
(52) U.S. Cl. ......................................................... 73/756
(58) Field of Classification Search ............. 73/700–756
See application file for complete search history.

(56) References Cited

U.S. PATENT DOCUMENTS

| | | | |
|---|---|---|---|
| 3,818,765 A | 6/1974 | Eriksen | |
| 4,141,252 A | 2/1979 | Lodge | |
| 4,415,858 A | 11/1983 | Hale | |
| 4,463,593 A | 8/1984 | Parker | |
| 4,695,551 A | 9/1987 | Samhaber et al. | |
| 4,700,560 A | 10/1987 | Hoffa et al. | |
| 4,786,474 A | 11/1988 | Cooper | |
| 5,178,267 A | 1/1993 | Grabenkort et al. | |
| 5,976,085 A | 11/1999 | Kimball et al. | |
| 6,883,377 B2 * | 4/2005 | Doubrovsky | 73/700 |
| 6,926,814 B2 | 8/2005 | Koenemann et al. | |
| 7,470,060 B1 * | 12/2008 | Hoben et al. | 374/143 |
| 7,540,197 B2 * | 6/2009 | Wavering et al. | 73/715 |
| 2002/0189363 A1 * | 12/2002 | Doubrovsky | 73/756 |
| 2003/0017078 A1 | 1/2003 | Trapp et al. | |
| 2007/0185472 A1 | 8/2007 | Baumfalk et al. | |
| 2008/0141780 A1 * | 6/2008 | Wavering et al. | 73/723 |

(Continued)

FOREIGN PATENT DOCUMENTS

DE    103 45 299 B3    7/2005
(Continued)

OTHER PUBLICATIONS

The French Search Report dated Oct. 7, 2009 in corresponding foreign application (FR0951600).
International Search Report/Written Opinion mailed May 13, 2009 in co-pending PCT application No. PCT/US 09/01616.

(Continued)

*Primary Examiner* — Andre Allen
(74) *Attorney, Agent, or Firm* — Nields, Lemack & Frame, LLC

(57) ABSTRACT

A device for determining a physical value of a liquid flowing in a pipe, without contact with the liquid. The device includes: a sensor for the physical value; a connector to insert into the pipe and including: an internal passage extending between two apertures, a flexible membrane for a pressure sensor, forming a wall of the internal passage; and a fastening mechanism for fastening the sensor onto the connector. The sensor is a temperature sensor fastened to the connector with the sensitive part of the sensor turned towards the membrane.

12 Claims, 6 Drawing Sheets

U.S. PATENT DOCUMENTS

| | | |
|---|---|---|
| 2008/0247906 A1 | 10/2008 | Heffels et al. |
| 2009/0214387 A1 | 8/2009 | Straub et al. |
| 2009/0247989 A1 | 10/2009 | Burke |
| 2009/0260438 A1* | 10/2009 | Hedtke .......................... 73/579 |
| 2009/0293625 A1* | 12/2009 | Sundet et al. ................... 73/708 |
| 2010/0015656 A1 | 1/2010 | Seitz et al. |
| 2010/0083731 A1* | 4/2010 | Hedtke .......................... 73/1.57 |

FOREIGN PATENT DOCUMENTS

| | | |
|---|---|---|
| EP | 1199556 A1 | 4/2002 |
| EP | 2 226 087 A1 | 9/2010 |
| GB | 1365769 | 9/1974 |
| WO | 2005/100957 A1 | 10/2005 |
| WO | 2007/131593 A1 | 11/2007 |
| WO | 2008/011876 A2 | 1/2008 |

OTHER PUBLICATIONS

European Communication mailed Sep. 13, 2011 in co-pending European patent application EP 09724042.8.
Office Action—Restriction—mailed Apr. 6, 2009 in co-pending U.S. Appl. No. 12/079,323.
Office Action mailed Jun. 26, 2009 in co-pending U.S. Appl. No. 12/079,323.
Final Rejection mailed Oct. 29, 2009 in co-pending U.S. Appl. No. 12/079,323.
Office Action mailed Jan. 5, 2012 in co-pending U.S. Appl. No. 12/079,323.
Final Rejection mailed Mar. 30, 2012 in co-pending U.S. Appl. No. 12/079,323.

* cited by examiner

DEVICE FOR DETERMINING A PHYSICAL VALUE OF A LIQUID FLOWING IN A PIPE

The invention relates to the determination of a physical value of a liquid flowing in a pipe, without contact with that liquid.

Circuits are known for certain liquids, in particular biological liquids, in which the components in contact with the liquids are single-use components.

To know the pressure of the liquid flowing in such a circuit, a connector has already been proposed for insertion in the pipe in which the liquid flows, that connector comprising an internal passage extending between two apertures for inlet/outlet; a flexible membrane forming a wall of that internal passage; and fastening means for a pressure sensor in order to attach the latter to the connector in a position in which its sensitive part is in contact with the flexible membrane.

Thanks to the flexible character of the membrane, the internal pressure of the connector (pipe pressure) may be transmitted to the pressure sensor.

The pressure sensor can be re-used whereas the connector inserted into the pipe is, like the pipe, a single use item.

The invention is directed to the provision of a device for determining the temperature of a liquid flowing in a pipe comprising, like the aforementioned device, a single use connector.

To that end it provides a device for determining a physical value of a liquid flowing in a pipe, without contact with said liquid, said device comprising:
  a sensor for said physical value;
  a connector to insert into said pipe and comprising:
    an internal passage extending between two apertures,
    a flexible membrane for a pressure sensor, forming a wall of said internal passage; and
  means for fastening said sensor onto said connector;
characterized in that said sensor is a temperature sensor fastened to said connector with the sensitive part of said sensor turned towards said membrane.

Thus, the device according to the invention uses, to determine the temperature, a connector similar to that of the aforementioned device to determine the pressure of the liquid, this connector comprising in particular a flexible membrane provided to cooperate with a pressure sensor.

Although it may seem surprising, the flexible membrane for a pressure sensor is also capable of cooperating with a temperature sensor, particularly but not exclusively by implementing the preferred features set out below.

The fact of using the same connector to determine the pressure of the liquid flowing in the pipe or to determine the temperature therein makes it possible to take advantage of economies of scale and a simplified implementation for a single-use circuit.

According to preferred features:
  said sensor comprises an infrared temperature probe; and a sheath enveloping said probe and comprising at one of its longitudinal ends, a stiff plate provided with an aperture; said plate being disposed between said membrane and said sensitive part to stiffen said membrane;
  said sensor comprises an obturating lid formed from an opaque film, said lid covering the face of said plate turned towards said membrane;
  said device comprises means for positioning said sensor relative to said connector in order for said lid to be in contact with a face of said membrane;
  said positioning means comprise a shoulder adapted to cooperate in abutment with a collar;
  said lid has constant emissivity in the temperature range from 4 to 40 degrees Celsius;
  said sheath comprises a cup and a cap assembled together by screwing;
  said cap comprises a breech of which the back is formed by said stiff plate;
  said probe comprises a head accommodating a converging lens;
  said fastening means comprise a tapping adapted to cooperate with a screw thread; and/or
  said connector is disposable whereas said sensor is reusable.

The disclosure of the invention will now be continued with the detailed description of an embodiment, given below by way of illustrative but non-limiting example, with reference to the accompanying drawings, in which.

Figure 1:
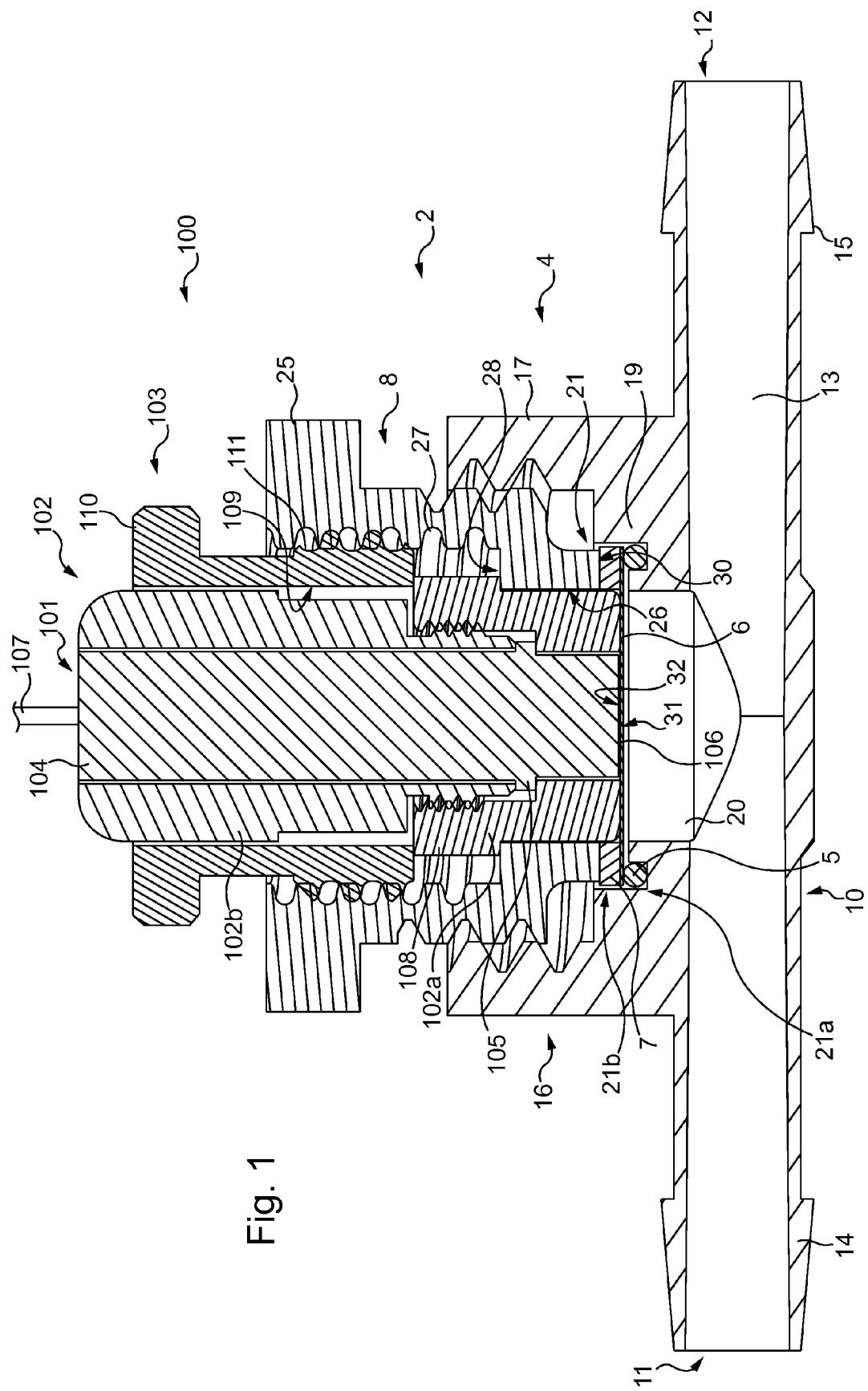
FIG. 1 is a cross-section of a device for determining the pressure of a liquid flowing in a pipe, the device being useful for the understanding of the invention.

The device illustrated in FIG. 1 makes it possible to determine the pressure of a liquid flowing in a pipe.

It comprises a disposable connector 2 to insert in a flexible pipe, also disposable, as well as a pressure sensor 100 adapted to be partially received in the connector 2.

Figure 3:
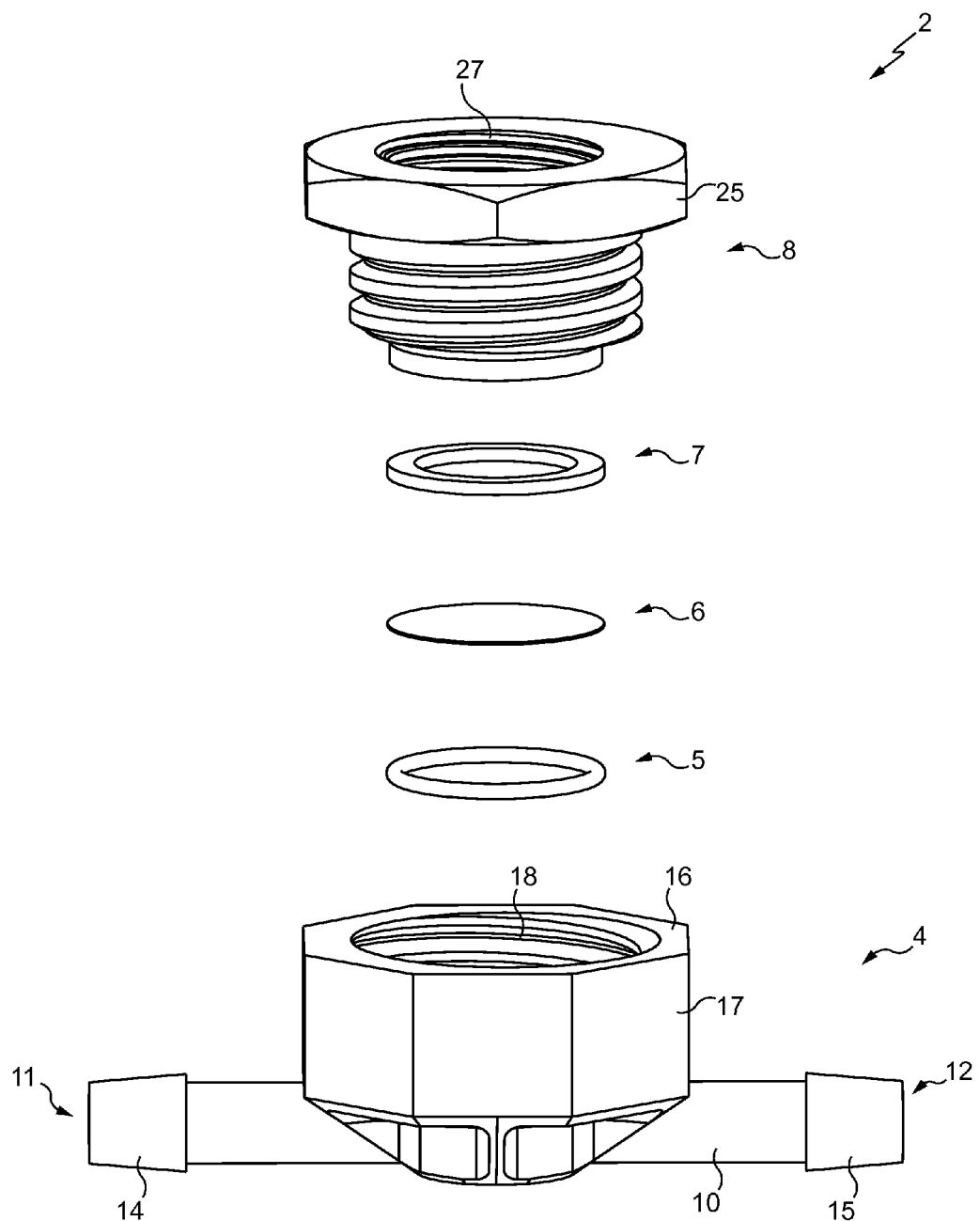
FIG. 3 is an exploded perspective view of the connector of the device of FIG. 1 and the device according to the invention.

The connector 2 will now be described more particularly, with the aid of FIGS. 1 and 3.

The connector 2 which is of T-shaped profile, is provided to be inserted in series in a disposable flexible pipe. It comprises base 4, an 'O' ring seal 5, a membrane 6, a stiff ring 7 and a tapped screw 8.

The base 4 is of molded plastics material (here a polypropylene copolymer that is resistant to gamma radiation). It comprises a straight pipe 10 forming an internal passage 13 extending between two apertures for inlet/outlet 11, 12 and enabling the liquid to flow inside the connector 2. This internal passage 13 is here of constant cross-section between the apertures 11 and 12.

To enable the insertion and the connection of the connector 2 between two sections of a disposable flexible pipe, two nipples 14, 15 are disposed at the apertures 11, 12 of the pipe 10.

The base 4 also comprises a bowl 16 which is disposed at the central part of the pipe 10.

The lateral wall 17 of the bowl 16 has an octagonal outer cross-section whereas its inner side forms a blind tapping 18 (FIG. 3) provided to cooperate with the screw 8.

The bottom 19 of that bowl 16 (FIGS. 1 and 3) comprises a cylindrical central bore 20 which issues into the internal passage 13. This bore 20 has a relatively large cross-section by virtue of which the liquid present in that bore 20 is continuously renewed (the liquid is not trapped in the bore 20).

On entering the bore 20 and over the whole of its periphery, the bottom 19 also comprises an annular recess 21 having an L-shaped cross-section.

This recess 21 thus forms a groove 21a adapted to accommodate the 'O' ring seal 5 and a bore 21b provided for the reception of the membrane 6 and of the stiff ring 7.

The seal 5 is an 'O' ring formed from an elastically deformable material (here silicone).

The membrane 6 is formed from a flexible film of single layer or multilayer plastics material (here linear low density polyethylene (LLDPE)).

The screw 8 is of molded plastics material (here a polypropylene copolymer that is resistant to gamma radiation). At its opposite end to its hexagonal head 25, it comprises a central cylindrical bore 26, of the same diameter as that of the bore 20.

Extending onwards from that bore 26, the screw 8 comprises a tapping 27 (FIGS. 1 and 3) of greater diameter which issues at its head 25.

The screw 8 also comprises an annular shoulder 28 situated at the junction between the bore 26 and the tapping 27.

The mounting of the connector 2 will now be described.

The first step consists of placing the 'O' ring seal 5, the membrane 6 and the stiff ring 7 in the base 4.

For this, the 'O' ring seal 5 is first of all inserted into the annular groove 21a. Next the membrane 6 is positioned such that it fully covers the entry of the bore 20 and the 'O' ring seal 5 (FIG. 1). Lastly, the stiff ring 7 is placed above the membrane 6.

The second step consists of screwing the screw 8 into the blind tapping 18 of the base 4 to fasten the membrane 6.

The screw 8 thus advances in the tapping 18 until its free end 30 comes into contact with the stiff ring 7.

The continuation of the screwing then leads to the compression of the 'O' ring seal 5, the stiff ring 7 making it possible to avoid the free end 30 of the screw 8 coming to rub directly against the membrane 6 which would risk deteriorating it.

Once the screw 8 has been tightened, the membrane 6 forms a wall of the internal passage 13.

The face 31 of this membrane 6 is thus in direct contact with the liquid flowing in the internal passage 13 while its opposite face 32 is isolated from that same internal passage 13.

The mounting of the connector 2 is thus terminated (FIG. 1), the membrane 6 being situated in register with the bore 26 and the tapping 27 of the screw 8.

The pressure sensor 100 will now be described.

This comprises a pressure probe 101, a generally cylindrical sleeve 102 enveloping the probe 101 and a hollow screw 103.

The pressure probe 101 comprises a cylindrical metal body 104, an annular collar 105 projecting at the periphery of the body 104 as well as a membrane 106 situated at one of the longitudinal ends of the body 104.

The body 104 houses a processing device which converts the movements of the membrane 106 into a signal representing the pressure.

At the opposite end to the membrane 106, the pressure probe 101 also comprises a flexible cable 107 to enable it to be supplied with power and ensure the transmission of the signals sent by the processing device.

The sleeve 102 is formed from a barrel 102a and a tube 102b screwed together and cooperating with the collar 105 to prevent translational movement of the probe 101 relative to the sleeve 102.

At the zone of screwing with the tube 102b the barrel 102a comprises a projecting collar 108 adapted to abut the shoulder 28 of the connector 2 to position the membrane 106 of the pressure probe 101 against the membrane 6.

The screw 103 comprises a through bore 109 of which the diameter is very slightly greater than the outer diameter of the tube 102b such that the screw is adapted to slide along that tube 102b.

On its outer face and at its opposite end to its circular head 110, the screw 103 has a screw thread 111 provided to cooperate with the tapping 27 of the connector 2, so as to provide the fastening of the pressure sensor 100 onto the connector 2.

The putting in place of the pressure sensor 100 in the connector 2 is carried out simply by disposing it such that its membrane 106 faces the membrane 6, and by inserting it into the tapping 27 and the bore 26 of the connector 2.

The movement continues until the collar 108 comes into abutment with the shoulder 28, the membrane 106 then resting against the face 32 of the membrane 6.

It then only remains to screw the screw 103 into the tapping 27 in order to provide the fastening of the sensor 100 in the connector 2.

The position in FIG. 1 (assembled device) is thus attained.

To operate the pressure determining device, the probe 101 of the sensor 100 is powered via the cable 107.

The liquid under pressure flowing in the connector 2 leads to the deformation of the membrane 6, the consequence of which is also to induce the deformation of the membrane 106 of the pressure sensor 100.

This deformation of the membrane 106 is converted by the probe 101 into a signal representing the pressure of the liquid flowing in the internal passage of the connector 2.

Figure 2:
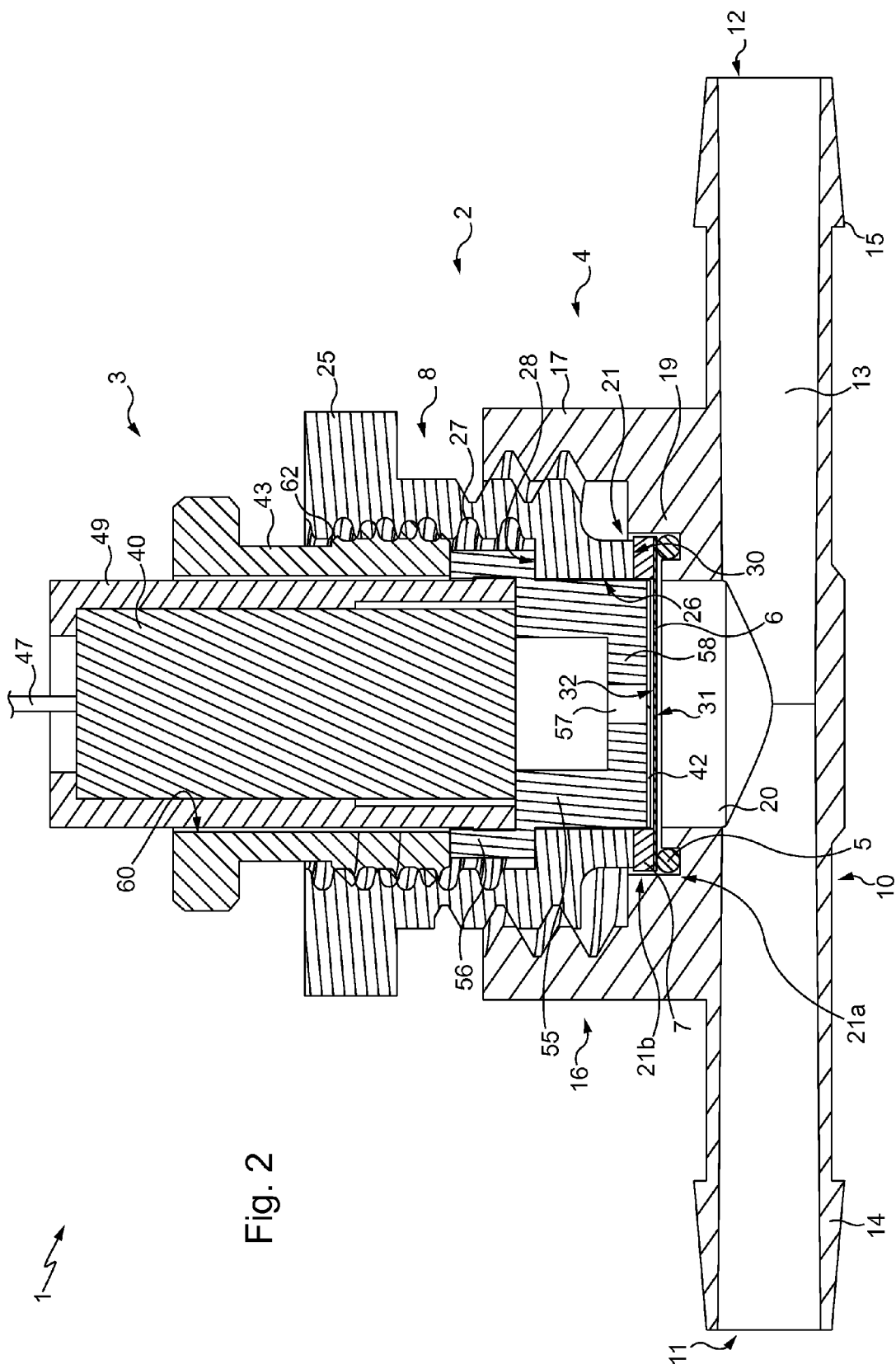
FIG. 2 is a cross-section of the device according to the invention.
Figure 4:
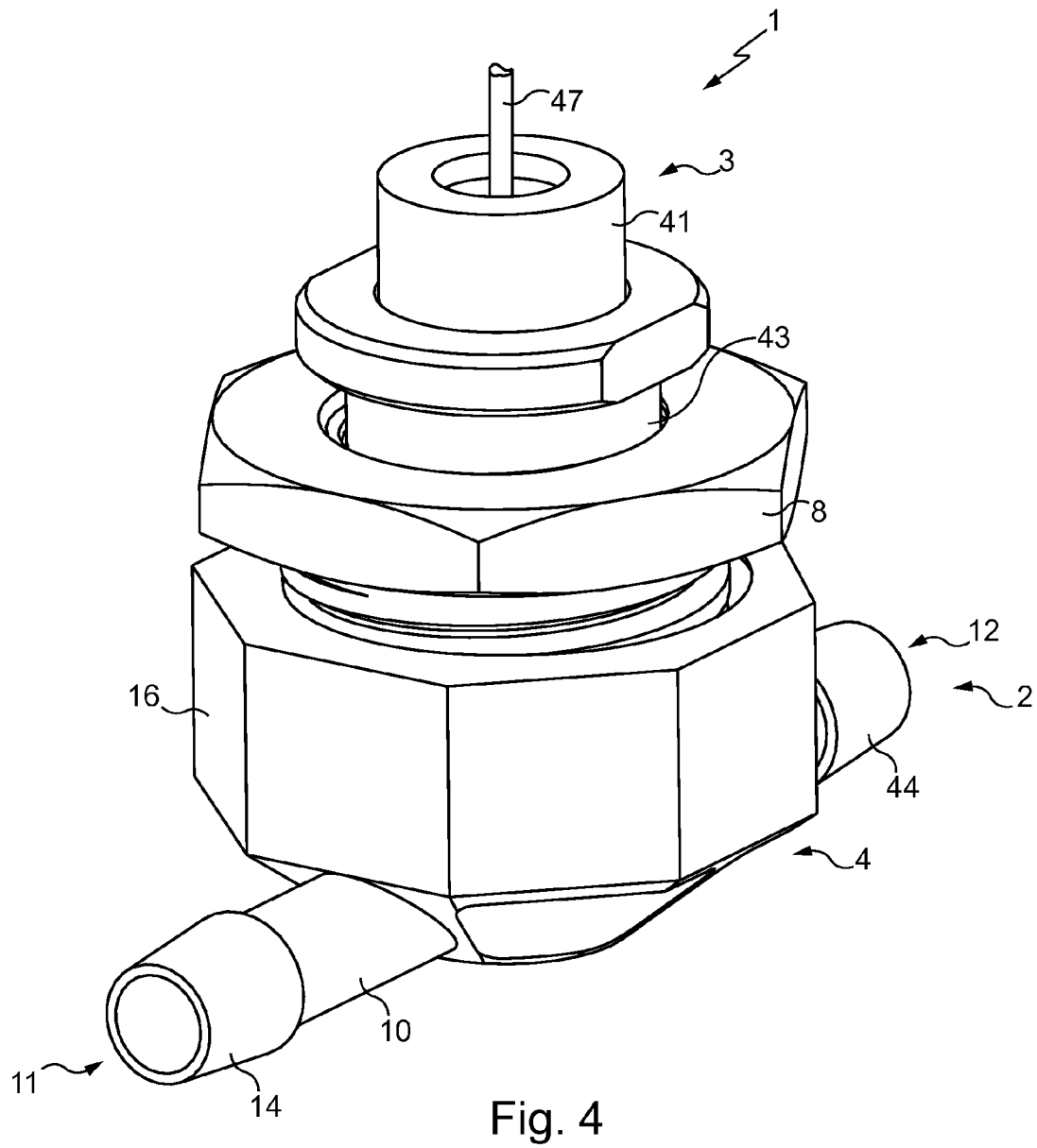
FIG. 4 is a perspective view of the device according to the invention.

The device 1 according to the invention and which is illustrated in the assembled state in FIGS. 2 and 4, makes it possible to determine, without contact, the temperature of a liquid flowing in a pipe.

It comprises a connector 2 as described earlier, but coupled here to a re-usable temperature sensor 3.

Figure 5:
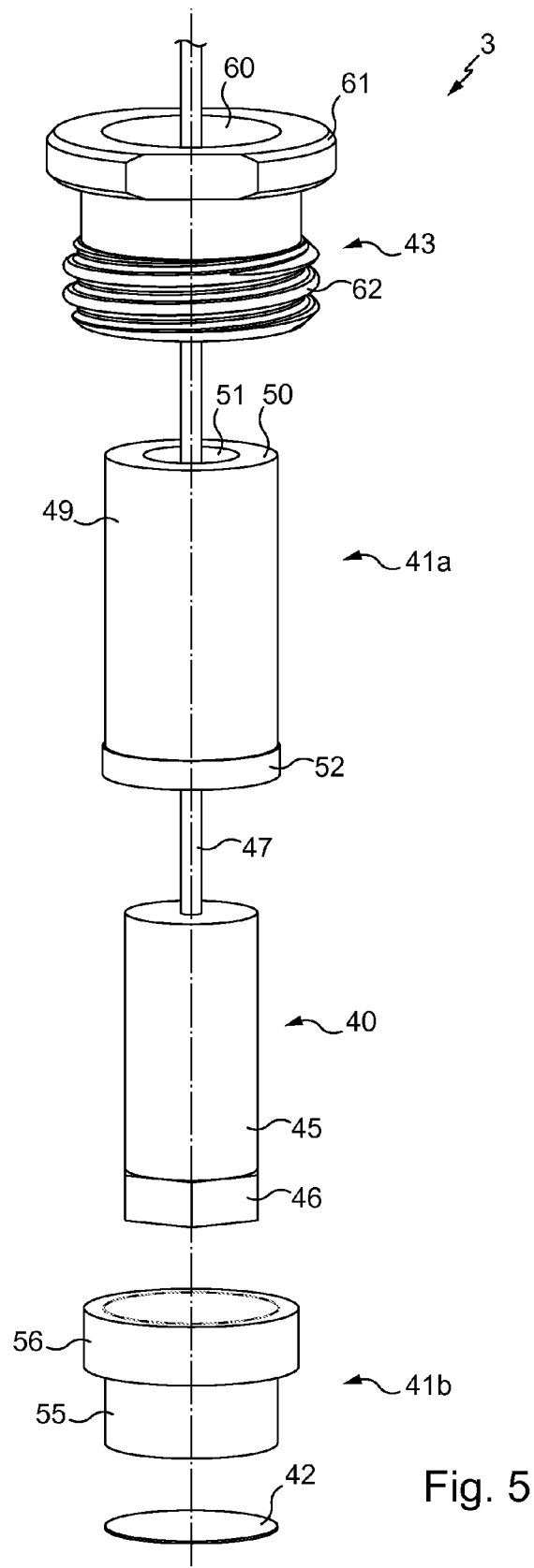
FIG. 5 is an exploded perspective view of the temperature sensor of the device according to the invention.

The sensor 3 will now be described with the aid of FIGS. 5 and 6.

The sensor 3 comprises a temperature probe 40, a sheath 41 enveloping said probe 40, an obturating lid 42 and a hollow screw 43 with a round flat head.

The temperature probe 40 comprises a generally cylindrical body 45 onto which is screwed a head 46 in the form of a hexagonal nut.

The body 45 and the head 46 of this probe 40 are hollow and each have an outer wall here of stainless steel.

The head 46 accommodates a converging lens enabling a detection cone to be defined of which the point (corresponding to the focal point of that lens) is situated on the lid 42 when the sensor 3 is assembled.

The body 45 houses a detector sensitive to infrared radiation as well as a processing device which converts the radiation captured by the sensor into a signal representing the temperature.

At the opposite end to the head 46, the probe 40 also comprises a flexible cable 47 to enable it to be supplied with power and ensure the transmission of the signals sent by the processing device.

The sheath 41 enveloping the probe comprises a cup 41a adapted to cooperate by screwing with a cap 41b The cup 41a comprises a cylindrical main wall 49 and a bottom wall 50.

The bottom wall 50 has a circular opening 51 provided for the passage of the cable 47 of the probe 40.

The cylindrical wall 49 has a screw thread 52 disposed on its outer face and at its opposite end to the bottom wall 50.

The cap 41b comprises a breech 55 surmounted by a tapped collar 56 provided to cooperate with the screw thread 52.

The back of the breech 55 forms a stiff plate 58 at the center of which a circular aperture 57 (FIG. 2) is formed to enable the passage of the infrared radiation towards the sensitive part of the detector of the probe 40.

The breech 55 furthermore has the same outer diameter as that of the cylindrical wall 49 of the cup 41a, this outer diameter moreover being slightly less than that of the central bore 26 of the screw 8 of the connector 2.

The obturating lid 42 is here formed from an opaque adhesive film (here of polyimide) of which the emissivity is constant in the temperature range from 4 to 40 degrees Celsius.

This lid 42, of the same diameter as the plate 58, is bonded to the latter so as to completely cover the face of that plate 58 that is oriented towards the membrane 6.

The screw 43 comprises a through bore 60 of which the diameter is very slightly greater than the outer diameter of the cylindrical wall 49 of the cup 41a such that the screw is adapted to slide along that cup 41a.

The screw 43 has on its outer face and at its opposite end to its circular head 61, a screw thread 62 provided to cooperate with the tapping 27 of the connector 2.

The assembly of the temperature sensor 3 is made in the following manner.

The cup 41a is first of all engaged in the bore 60 of the screw 43, then the end of the cable 47 is inserted inside that cup 41a so as to make it come out by the opening 51.

Next the probe 40 is disposed in the cup 41a and lastly the cap 41b is screwed onto that cup.

Figure 6:
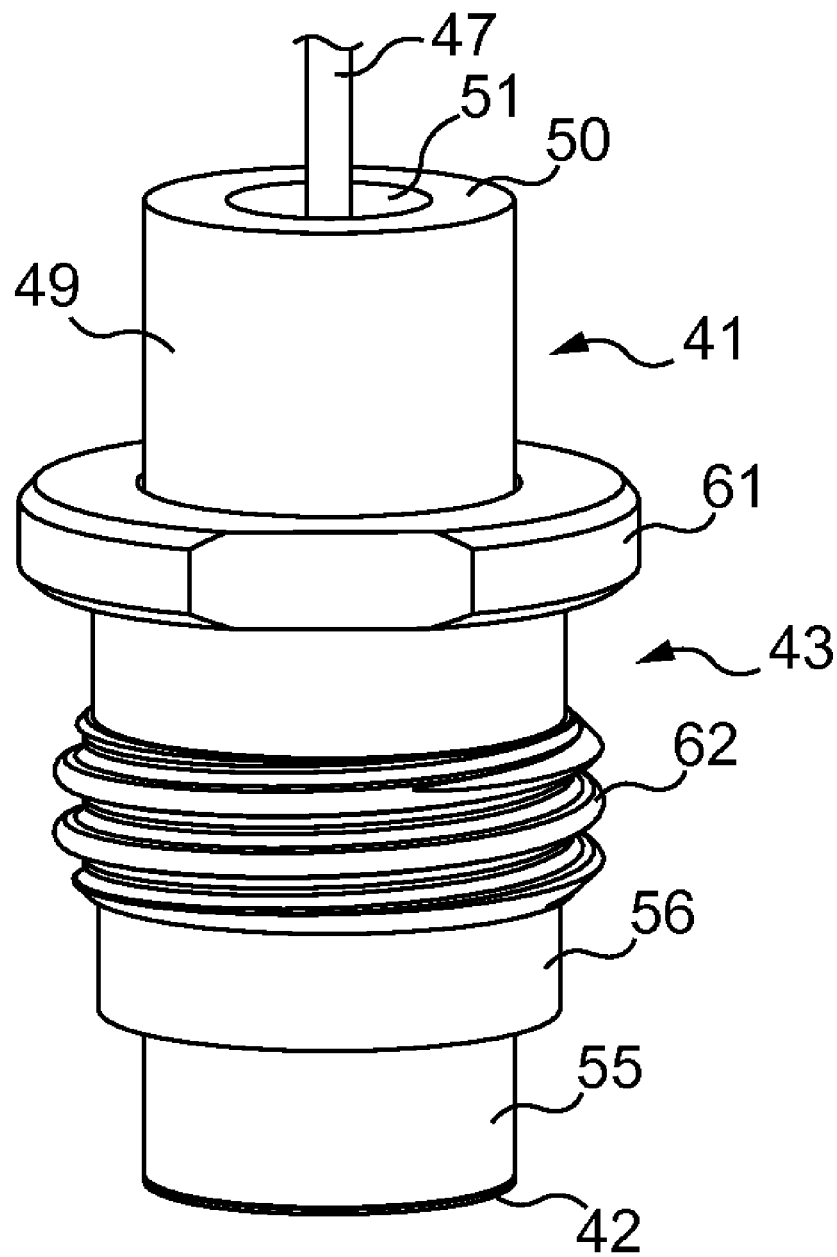
FIG. 6 is a perspective view of the temperature sensor of FIG. 5 in the assembled state.

Once assembled, the temperature sensor 3 is as illustrated in FIG. 6 and is then adapted to be received partially in the connector 2.

For this, the sensor 3 is disposed such that the lid 42 faces the membrane 6, and sensor 3 is inserted into the tapping 27 and the bore 26 of the connector 2.

The movement continues until the collar 56 comes into abutment with the shoulder 28 (FIG. 2), the lid 42 then resting against the face 32 of the membrane 6.

It then only remains to screw the screw 43 into the tapping 27 in order to provide the fastening of the sensor 3 in the connector 2.

The position of FIG. 2 is thus attained in which the device 1 is in the assembled state in which the sensor 3 is fastened to the connector 2 with the sensitive part of the detector of the probe 40 being turned towards the membrane 6.

It will be noted that the cooperation of the collar 56 and of the annular shoulder 28 enables reproducible positioning of the lid 42 to be provided. This avoids any accidental tearing of the membrane 6 which could lead to the contamination of the temperature sensor 3 (which is re-usable) by the liquid flowing in the internal passage 13 of the connector 2.

To operate the device 1, the probe 40 of the sensor 3 is powered via the cable 47. The infrared radiation emitted by the lid 42 after passage through the lens 46, enters the sensitive part of the detector.

This radiation is converted by the processing device into a signal representing the temperature which is transmitted via the cable 47.

The presence of a converging lens in the head 46 of the probe 40 enables the diameter of the aperture 57 to be limited in order for the lid 42 to have a maximum area in contact with the plate 58 of the breech 55, which is stiff.

The lid 42 and the membrane 6 are thus stiffened by that plate 58 which avoids any risk of bursting of the membrane 6, even in the case of high pressure of the liquid flowing in the internal passage 13 of the connector 2.

The analysis by the sensor 3 of the emission from that lid 42 enables the temperature thereof to be determined with improved precision in that the coefficient of emissivity of that lid is constant in the temperature range of interest here, i.e. between 4 and 40 degrees Celsius.

Due to the very small thickness of the lid 42, its temperature is the same as that of the membrane 6 against which that lid 42 is pressed.

In similar manner and on account of the very small thickness of the membrane 6, its temperature is the same as that of the liquid under pressure with which that membrane 6 is in contact.

The sensor 3 thus enables the temperature of the liquid flowing in the internal passage 13 to be determined, here with a precision of +/−2 degrees.

In a variant not represented of the device according to the invention, the sensor does not comprise a lid, the temperature measurement being made directly on the membrane or through it.

In another variant not represented, the sensor does not comprise a wall, such as the plate 58, to stiffen the membrane (the pressure of the liquid flowing in the internal passage of the connector being low).

In still other variants not represented:
  there is no cable such as 47 or 117, and instead there is provided (i) a battery, coupling (magnetic, capacitive, . . . ) means or other powering means and (ii) wireless communication and memory device such as a RFID chip or Bluetooh or Zigbee enabled device to communicate remotely with a processor device;
  the probe does not comprise a lens and/or the aperture in the sheath has a greater diameter;
  the temperature ranges are different and/or the emissivity of the lid varies as a function of the temperature; and/or
  the sensor comprises a probe other than an infrared probe (for example a thermocouple in contact with the membrane).

Numerous other variants are possible according to circumstances, and in this connection it is to be noted that that the invention is not limited to the example embodiments described and shown.

The invention claimed is:

1. A device for determining a physical value of a liquid flowing in a pipe, without contact with said liquid, said device comprising:
  a sensor for sensing said physical value;
  a connector to insert into said pipe and comprising:
    an internal passage extending between two apertures,
    a flexible membrane adapted to cooperate with a pressure sensor to determine the pressure of said flowing liquid, and also adapted to cooperate with a temperature sensor to determine the temperature of said flowing liquid, said flexible membrane forming a wall of said internal passage; and
  means for fastening said sensor onto said connector;
  wherein said sensor is a temperature sensor fastened to said connector with the sensitive part of said sensor turned towards said membrane.

2. A device according to claim 1, wherein said sensor comprises an infrared temperature probe; and a sheath enveloping said probe and comprising at one of its longitudinal ends, a stiff plate provided with an aperture; said plate being disposed between said membrane and said sensitive part to stiffen said membrane.

3. A device according to claim 2, wherein said sensor comprises an obturating lid formed from an opaque film, said lid covering the face of said plate turned towards said membrane.

4. A device according to claim 3, wherein it comprises means for positioning said sensor relative to said connector in order for said lid to be in contact with a face of said membrane.

5. A device according to claim 4, wherein said positioning means comprise a shoulder adapted to cooperate in abutment with a collar.

6. A device according to claim 3, wherein said lid has constant emissivity in the temperature range from 4 to 40 degrees Celsius.

7. A device according to claim 2, wherein said sheath comprises a cup and a cap assembled together by screwing.

8. A device according to claim 7, wherein said cap comprises a breech of which the back is formed by said stiff plate.

9. A device according to claim 1, wherein said sensor comprises an infrared temperature probe, and said probe comprises a head accommodating a converging lens.

10. A device according to claim 1, wherein said fastening means comprise a tapping adapted to cooperate with a screw thread.

11. A device according to claim 1, wherein said connector is disposable whereas said sensor is re-usable.

12. A device according to claim 1, wherein said connector has a T-shaped profile.

* * * * *